United States Patent
Sugimura et al.

(10) Patent No.: US 6,589,632 B1
(45) Date of Patent: Jul. 8, 2003

(54) LIQUID-IMPERVIOUS BACKSHEET FOR BODY FLUIDS DISPOSAL ARTICLE

(75) Inventors: Toru Sugimura, Kagawa-ken (JP); Takamitsu Igaue, Kagawa-ken (JP); Shigeo Imai, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/512,654

(22) Filed: Feb. 24, 2000

(30) Foreign Application Priority Data

Mar. 3, 1999 (JP) ............................ 11-055487

(51) Int. Cl.[7] .............................. B32B 3/00; B32B 3/10; B32B 3/12; B32B 3/26; A61F 13/20

(52) U.S. Cl. ..................... 428/174; 428/131; 428/137; 428/138; 428/141; 428/158; 428/166; 428/304.4; 428/315.5; 428/913; 604/358; 604/370; 604/379; 604/383; 604/385.01; 604/385.08

(58) Field of Search ............................ 604/385.01, 379, 604/370, 358, 383, 385.08; 428/174, 138, 141, 131, 137, 913, 158, 166, 304.4, 315.5

(56) References Cited

U.S. PATENT DOCUMENTS

| | | | |
|---|---|---|---|
| 3,881,489 A | * 5/1975 | Hartwell | 128/287 |
| 3,989,867 A | 11/1976 | Sisson | 428/132 |
| 4,306,559 A | * 12/1981 | Nishizawa | 128/287 |
| 4,341,216 A | * 7/1982 | Obenour | 128/287 |
| 4,591,523 A | * 5/1986 | Thompson | 428/131 |
| 4,681,793 A | 7/1987 | Linman et al. | 428/138 |
| 4,824,718 A | * 4/1989 | Hwang | 428/284 |
| 5,158,819 A | 10/1992 | Goodman, Jr. et al. | 428/131 |
| 5,441,691 A | 8/1995 | Dobrin et al. | 264/504 |
| 5,567,376 A | 10/1996 | Turi et al. | 264/455 |
| 5,681,301 A | * 10/1997 | Yang et al. | 604/370 |

FOREIGN PATENT DOCUMENTS

| | | |
|---|---|---|
| JP | 5-200063 | 8/1993 |
| WO | 96/00548 | 1/1996 |
| WO | 97/24096 | 7/1997 |
| WO | 98/42289 | 10/1998 |

* cited by examiner

Primary Examiner—Harold Pyon
Assistant Examiner—Catherine A. Simone
(74) Attorney, Agent, or Firm—Lowe Hauptman Gilman & Berner, LLP

(57) ABSTRACT

A liquid-impervious backsheet for body fluids disposal article having upper and lower surfaces made of thermoplastic synthetic resin, the sheet includes a plurality of independent concave zones depressed downward from the lower surface and a smooth zone extending around these concave zones, each of the concave zones being formed in its region except its peripheral edge with at least one micropore.

12 Claims, 3 Drawing Sheets

US 6,589,632 B1

LIQUID-IMPERVIOUS BACKSHEET FOR BODY FLUIDS DISPOSAL ARTICLE

BACKGROUND OF THE INVENTION

This invention relates to a liquid-impervious backsheet for a body fluids disposal article such as a disposable diaper or a sanitary napkin.

Japanese Patent Application Disclosure No. 1993-200063 disclose a breathable liquid-impervious backsheet of a disposable diaper having, at least on one surface thereof, rough surface regions comprising a plurality of microprotuberances formed by grains of inorganic filler and relatively smooth surface regions wherein the rough surface regions include breathable micropores each having a diameter of 0.03~5 $\mu$m.

With this known sheet, the rough surface regions are intended to conceal an absorbent core of the article soiled with body fluids and the smooth surface regions having a see through property are intended to tell the article user of a proper timing for exchanging the used article with a fresh one.

The Japanese Patent Application Disclosure No. 1993-200063 discloses such sheet particularly as used as the backsheet of the disposable diaper. The rough surface regions partially underlie the absorbent core and, in such zones, the absorbent core may cover the micropores to make their breathability ineffective. On the other hand, some of the micropores crowded in the rough surface regions may be connected one to another until they form a pore having a sufficiently large diameter to be moisture-pervious and consequently the body fluids may leak therethrough.

SUMMARY OF THE INVENTION

It is an object of this invention to provide an improved liquid-impervious backsheet adapted to maintain a desired breathability and, at the same time, to prevent body fluids from leaking.

According to this invention, there is provided an improvement of liquid-impervious backsheet for a body fluids disposal article having upper and lower surface and made of thermoplastic synthetic resin.

The improvement of this invention is in that the sheet comprises a plurality of independent concave zones depressed downward from the lower surface and a smooth zone extending around said concave zones, each of the concave zones is formed except a peripheral edge thereof with at least one micropore.

According to one embodiment of this invention, at least an upper surface of the sheet is water repellent in the concave zones and at least the upper surface of said sheet is hydrophilic in the smooth zone.

According to another embodiment of this invention, the number of the concave zones per 10 cm$^2$ of the sheet is in a range of 4~100, a throat-area of each of the concave zones is in a range of 0.002~2.0 cm$^2$, an intercentral distance of each pair of adjacent the concave zones is in a range of 0.1~1.5 cm and a height as measured from the lower surface of the sheet to a lower surface of a bottoms in each of the concave zones is in a range of 0.01~0.3 cm.

According to still another embodiment of this invention, a thickness of the sheet is in a range of 10~100 $\mu$m and an inner diameter of each of the micropores is in a range of 0.05~1.0 mm.

DETAILED DESCRIPTION OF THE PREFERRED EMBODIMENTS

Details of a liquid-impervious backsheet for a body fluids disposable article according to this invention will be more fully understood from the description given hereunder with reference to the accompanying drawings.

Figure 1:
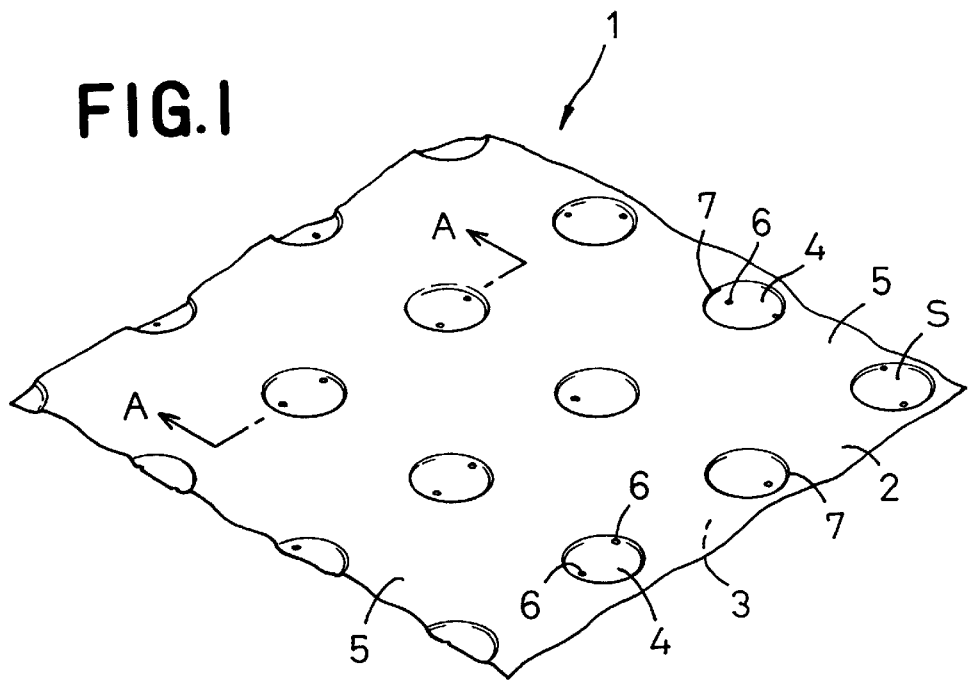
FIG. 1 is a scale-enlarged perspective view of a liquid-impervious backsheet according to this invention.
Figure 2:
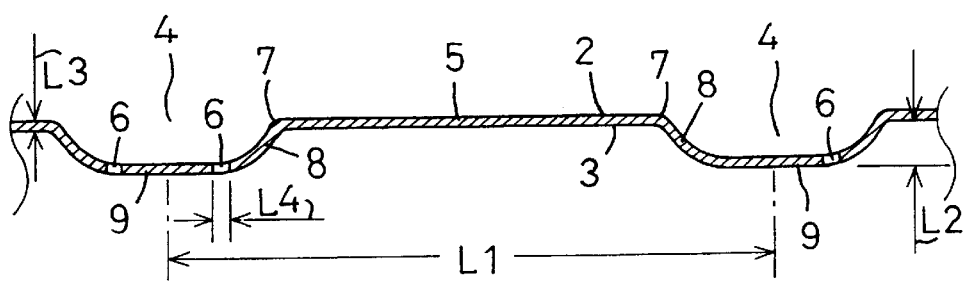
FIG. 2 is a sectional view taken along a line A—A in FIG. 1.

FIG. 1 is a scale-enlarged perspective view of a liquid-impervious backsheet 1 and FIG. 2 is a sectional view taken along a line A—A in FIG. 1. The sheet 1 is made of hydrophobic thermoplastic synthetic resin having a high flexibility and a thickness L3 of 10~100 $\mu$m. The sheet 1 has upper and lower surfaces 2, 3 and comprises a plurality of independent concave zones 4 each depressed downward from the lower surface 3 and a smooth zone 5 continuously extending around the concave zones 4. The sheet 1 is locally water repellent finished and locally hydrophilicized. More specifically, the upper surface 2 of the sheet 1 is water repellent in the concave zones 4 and hydrophilic in the smooth zone 5.

The concave zones 4 are uniformly sized and orderly arranged substantially at regular intervals. Each of the concave zones 4 has a circular peripheral edge 7 and one or two breathable micropore(s) extending through the sheet 1 between the upper and lower surfaces 2, 3 in a region except the circular peripheral edge 7. It is possible without departing from the scope of this invention to form the concave zone 4 with more than two micropores 6. While the circular peripheral edge 7 is illustrated to taper from its upper end toward its lower end, it is also possible without departing from the scope of this invention to provide the circular peripheral edge 7 which is substantially vertical or flares from its upper end toward its lower end.

The number of the concave zones 4 per 10 cm$^2$ of the sheet 1 is in a range of 4–100 and an opening area defined inside the peripheral edge 7 of each concave zone 4 is in a range of 0.002–2.0 cm$^2$, preferably 0.2–2.0 cm$^2$. Assumed that the number of the concave zones 4 is less than four and the opening area is smaller than 0.002 cm$^2$, the concave zones 4 will be too sparsely distributed and the body fluids discharged onto the article will rapidly spread over the smooth zone 5 without being obstructed by the concave zones 4. As a result, a partial amount of body fluids may reach the edges of the panel 1 and even leak therefrom before reabsorbed by the absorbent core and the other members (not shown). Assumed that the number of the concave zones 4 exceeds ten or the opening area is larger than 2.0 cm$^2$, the concave zones 4 will be too crowded or an area ratio of the concave zones 4 to the sheet 1 will become unacceptably high. Consequently, the concave zones 4 may prevent the body fluids from spreading over the smooth zone 5.

Each of the concave zones 4 has a dish-like shape defined by the peripheral edge 7, a gently curved spherical side wall 8 and substantially flat bottom 9. The concave zone 4 according to this invention is not limited to such a dish-like shape but may be realized in the other shape such as cone- or truncated cone-shape, or cylindrical shape. Each pair of adjacent concave zones 4 has an intercentral distance L1 of 0.1~1.5 cm. Assumed that the intercentral distance is less than 0.1 cm, the concave zones 4 will be too crowded and may prevent the body fluids from smoothly spreading. Assumed that the intercentral distance is larger than 1.5 cm, distribution of the concave zones 4 will become too sparse depending on the throat-area of each concave zone 4 and, as has already been described, a partial amount of the body fluids may rapidly spread and reach the edges of the sheet 1. This may cause leakage of the body fluids.

A height L2 as measured from the lower surface 3 of the sheet 1 to the lower surface 3 of the bottom in each concave zone 4 is in a range of 0.01~0.3 cm. Assumed that this height L2 is less than 0.01 cm, a difference in level between the smooth zone 5 and the concave zones 5 will become too small and correspondingly facilitate the body fluids to flow into the respective concave zones 4. Assumed that the height L2 exceeds 0.3 cm, a touch of the sheet 1 will be deteriorated.

Each of the micropores 6 has a diameter L4 of 0.05~1.0 mm. The diameter L4 less than 0.05 mm will adversely affect the breathability. The diameter L4 larger than 1.0 mm will allow an amount of moisture to flow through the micropore 6 and may cause leakage of body fluids.

Figure 3:
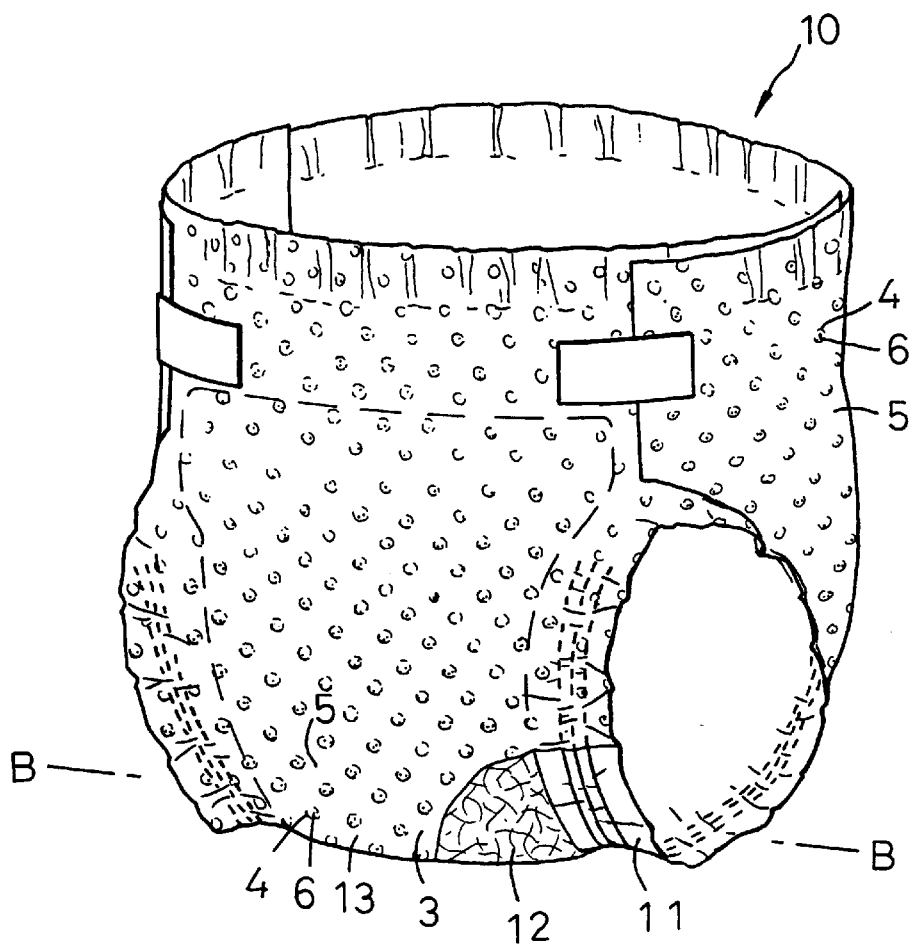
FIG. 3 is a perspective view showing a disposable diaper using the sheet according to this invention.
Figure 4:
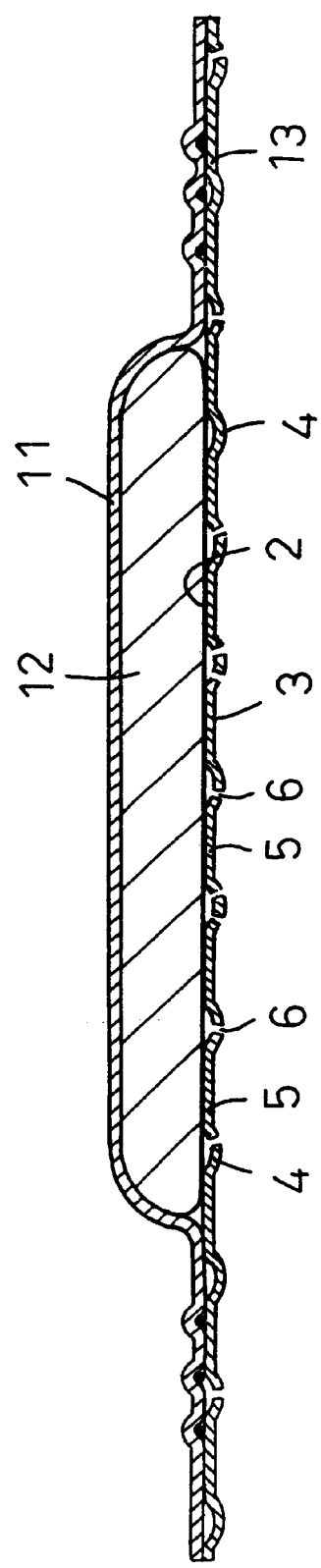
FIG. 4 is a sectional view taken along a line B—B in FIG. 3.

FIG. 3 is a perspective view showing a disposable diaper using the sheet 1 according to this invention and FIG. 4 is a sectional view taken along a line B—B in FIG. 3. FIG. 3 shows a partially cutaway diaper 10 assembled to be ready for wearing. As shown, the sheet 1 is used as a backsheet 13 of the diaper 10. The diaper 10 comprises a liquid-pervious topsheet 11, a liquid-impervious backsheet 13 and a liquid-absorbent core 12 disposed between these two sheets 11, 13. The upper surface 2 of the backsheet 13 underlying the lower surface of the absorbent core 12 so that the smooth zone 5 is in contact with the absorbent core 12 but the concave zones 5 as well as the micropores 6 are spaced from the lower surface of the absorbent core 12. Excretion such as urine, loose passage or the like exuding from the absorbent core 12 spreads over the hydrophilic smooth zone 5 and then is reabsorbed by the absorbent core 12 in a region of the absorbent core 12 other than the region in which the excretion has exuded. The concave zones 4 are water repellent and therefore it is not concerned that the spreading excretion might flow into the concave zones 4. In this manner, the sheet 1 can maintain its desired breathability.

The sheet 1 may be treated so that both its upper and lower surfaces 2, 3 present water repellent property in the concave zones 4 and has hydrophilic nature in the smooth zone 5. However, neither the water repellent treatment nor the hydrophilicizing treatment is essential for the sheet 1. Even when the sheet 1 is subjected to none of such treatments, it will not be concerned that the absorbent core 12 might cover the micropores 6 and affect the desired breathability because the micropores 6 formed in the concave zones 4 are kept spaced from the absorbent core 12 as best seen in FIG. 4.

Suitable stock material for the sheet 1 may be selected from a group consisting of polyolefine plastic sheets such as a polyethylene sheet and a polypropylene sheet, and a polyamide plastic sheet and a polyester plastic sheet.

The sheet 1 can be formed with the concave zones 4 and the breathable micropores 6, for example, by so-called corona discharge treatment. Apparatus for this treatment comprises a discharge electrode adapted to repeat pulsating corona discharge and a roll provided on its peripheral surface with a plurality of protuberances and covered with dielectric. The discharge electrode is spaced by a given distance from and opposed to the roll covered with dielectric and the sheet 1 is sticked fast to the roll with the lower surface 3 of the sheet 1 outside so that an air gap may be maintained between the lower surface 3 and the discharge electrode. As rotation of the roll transports the sheet 1, a dielectric breakdown locally occurs between the discharge electrode and the protuberances on the roll. Thus the pulsating corona discharge repeatedly occurs from the discharge electrode to the protuberances. In this manner, current discharged from the discharge electrode to the protuberances form the sheet 1 with the micropores 6 and, at the same time, the protuberances are heated by the corona discharged to form the sheet 1 with the concave zones 4.

The sheet 1 formed with the concave zones 4 and the smooth zone 5 in this manner may be then subjected to water repellent and hydrophilicizing treatment, for example, by a printing technique in which the concave zones 4 and the smooth zone 5 are respectively coated with suitable kinds of surfactant using a coating plate having a surface pattern in conformity with a pattern defined by the concave zones 4 and smooth zone 5 on the sheet 1.

This invention is applicable to, in addition to the backsheet of disposable diaper, to the backsheet of sanitary napkin.

The liquid-impervious backsheet according to this invention has the concave zones and the smooth zone wherein the concave zones are formed with the breathable micropores. Such an arrangement reliably eliminates a concern that the absorbent core and the other members directly overlying the absorbent core might cover the micropores and affect the breathability desired for these micropores.

With the embodiment in which the concave zones are water repellent and the smooth zone is hydrophilic, after having spread over the smooth zone, the body fluids are reabsorbed by the absorbent core. It is not concerned that the body fluids might flow into the concave zones and fill the micropores. Therefore, the breathability desired for these micropores can be ensured and leakage of the body fluids can be reliably avoided.

The liquid-impervious backsheet according to this invention, on the whole, comprises convex and concave surfaces contributing to improvement in a cushioning effect of the article.

What is claimed is:

1. A liquid-impervious backsheet for a body fluid disposal article, said backsheet having upper and lower surfaces and made of thermoplastic synthetic resin, said liquid-impervious backsheet comprising a plurality of independent concave zones depressed downward in a direction from said upper surface to said lower surface, and a substantially flat zone extending around said concave zones, each of said concave zones being formed with at least two micropores, each of said micropores extending from said upper surface to said lower surface; wherein the upper surface of said backsheet is water repellent in said concave zones and hydrophilic in said substantially flat zone.

2. The liquid-impervious backsheet according to claim 1, wherein the number of said concave zones per 10 cm$^2$ of said backsheet is in a range of 4~100, an area defined by a peripheral edge of each of said concave zones is in a range of from about 0.002 to about 2.0 cm$^2$, a distance between centers of said concave zones which are adjacent to each other is in a range of from about 0.1 to about 1.5 cm, and a height as measured from the lower surface of said backsheet in the substantially flat zone to the lower surface of said backsheet at a bottom of each of said concave zones is in a range of from about 0.01 to about 0.3 cm.

3. The liquid-impervious backsheet according to claim 1, wherein a thickness of said backsheet is in a range of from about 10 to about 100 μm and an inner diameter of each of said micropores is in a range of from about 0.05 to about 1.0 mm.

4. A liquid-impervious backsheet for a disposable garment, said backsheet having upper and lower surfaces, said backsheet comprising a plurality of independent concave zones depressed downward in a direction from said upper surface to said lower surface; wherein a remaining zone of said backsheet where the concave zones are not formed extends around said concave zones;

each of said concave zones is formed with at least one micropore extending from said upper surface to said lower surface; and the upper surface of said backsheet is water repellent in said concave zones and hydrophilic in the remaining zone of said backsheet.

5. The backsheet of claim 4, wherein said backsheet is made of a thermoplastic synthetic resin.

6. The backsheet of claim 4, wherein the remaining zone of said backsheet is substantially flat.

7. The backsheet of claim 4, wherein each of said concave zones is formed with at least two said micropores.

8. The backsheet of claim 4, wherein the number of said concave zones per 10 $cm^2$ of said backsheet is in a range of 4~100, an area defined by a peripheral edge of each of said concave zones is in a range of from about 0.002 to about 2.0 $cm^2$, a distance between centers of adjacent said concave zones is in a range of from about 0.1 to about 1.5 cm, and a height as measured from the lower surface in the remaining zone to the lower surface at a bottom of each of said concave zones is in a range of from about 0.01 to about 0.3 cm.

9. The backsheet of claim 4, wherein a thickness of said backsheet is in a range of from about 10 to about 100 mm and an inner diameter of each of said micropores is in a range of from about 0.05 to about 1.0 mm.

10. The backsheet of claim 4, wherein each of said concave zones has a curved side wall and a substantially flat bottom, and said micropore is formed in said bottom.

11. The backsheet of claim 4, wherein said concave zones are substantially identical in shape.

12. The backsheet of claim 4, wherein said concave zones have a shape selected from the group consisting of cone, truncated cone, and cylinder.

* * * * *